United States Patent
Schweitzer et al.

(10) Patent No.: US 12,303,961 B2
(45) Date of Patent: May 20, 2025

(54) INSTRUMENT PRE-PRODUCT AND MEDICAL INSTRUMENT

(71) Applicant: Aesculap AG, Tuttlingen (DE)

(72) Inventors: Tom Schweitzer, Tuttlingen (DE); Corvin Motz, Pfullendorf (DE); Andreas Deutschendorf, Spaichingen (DE)

(73) Assignee: Aesculap AG, Tuttlingen (DE)

( * ) Notice: Subject to any disclaimer, the term of this patent is extended or adjusted under 35 U.S.C. 154(b) by 366 days.

(21) Appl. No.: 17/897,173

(22) Filed: Aug. 28, 2022

(65) Prior Publication Data
US 2022/0410245 A1 Dec. 29, 2022

Related U.S. Application Data

(63) Continuation of application No. PCT/EP2021/055357, filed on Mar. 3, 2021.

(30) Foreign Application Priority Data

Mar. 5, 2020 (DE) .................... 10 2020 105 886.1

(51) Int. Cl.
*B21D 53/00* (2006.01)
*A61B 17/00* (2006.01)
(Continued)

(52) U.S. Cl.
CPC ............ *B21D 53/00* (2013.01); *A61B 17/062* (2013.01); *A61B 2017/00858* (2013.01); *A61B 2017/2825* (2013.01)

(58) Field of Classification Search
CPC ........ A61B 17/062; A61B 2017/00858; A61B 2017/2825
See application file for complete search history.

(56) References Cited

U.S. PATENT DOCUMENTS 2,597,394 A 5/1952 Snowden
5,213,093 A * 5/1993 Swindle ............... A61B 1/0011
600/920
(Continued)

FOREIGN PATENT DOCUMENTS

CN 103386525 A 11/2013
DE 3219260 A1 11/1983
(Continued)

OTHER PUBLICATIONS

Written Opinion received in International Application No. PCT/EP2021/055357 dated May 18, 2021, with translation, 17 pages.
(Continued)

*Primary Examiner* — Erin McGrath
(74) *Attorney, Agent, or Firm* — Christopher A. Rothe; CM Law

(57) ABSTRACT

A medical instrument and a semi-finished instrument. The semi-finished instrument includes an instrument body part blank for forming an instrument body part of the medical instrument. The instrument body part blank is made of a metal, in particular an instrument steel. The semi-finished instrument also includes a distal end region and a recess on the distal end region for accommodating a hard metal element. The recess has an abutment face for the hard metal element. The instrument body part blank includes a solder chamber for accommodating solder. The solder chamber is fluidically connected to the recess.

20 Claims, 8 Drawing Sheets

Figure 1:
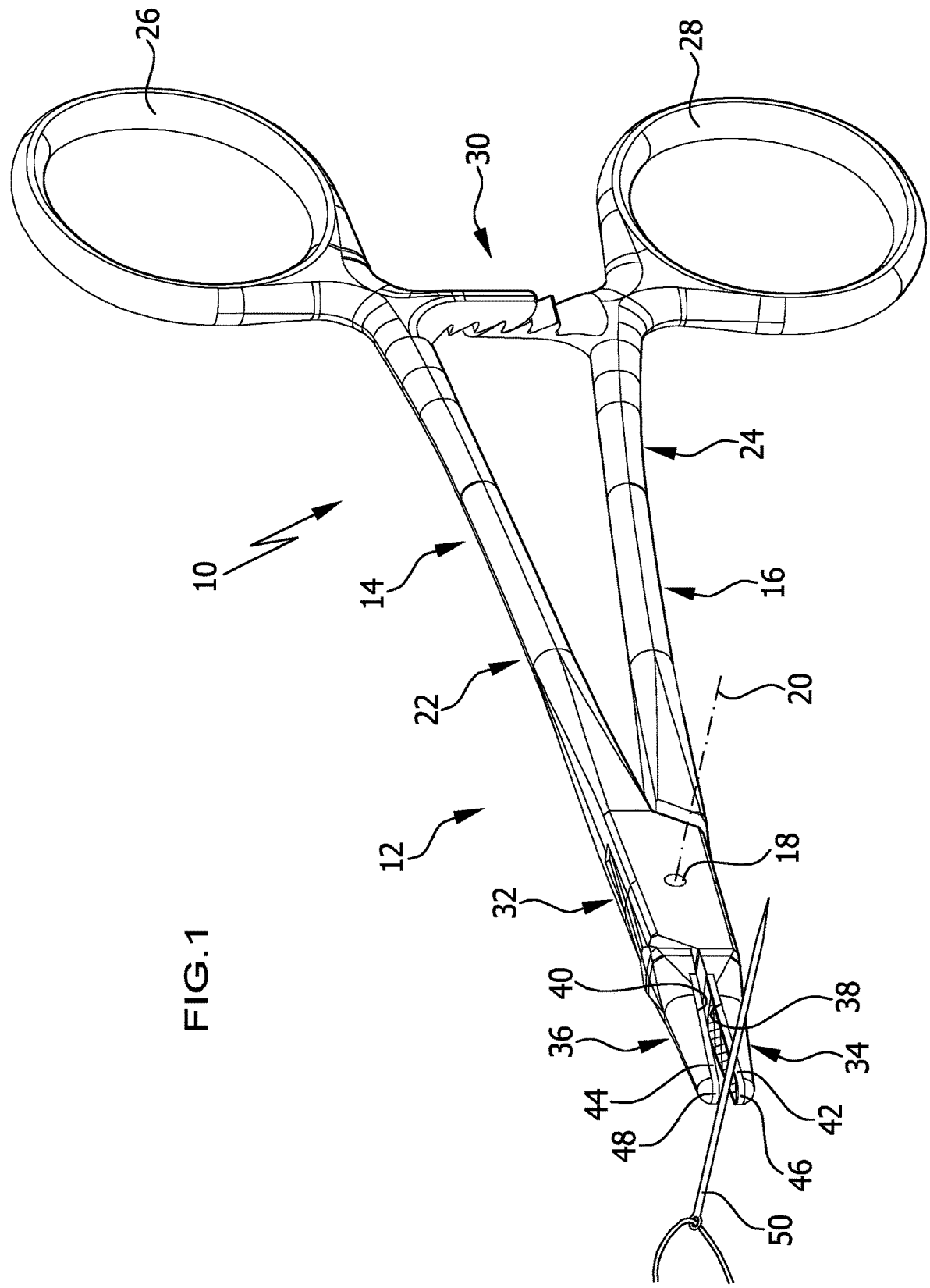

(51) Int. Cl.
*A61B 17/062* (2006.01)
*A61B 17/28* (2006.01)

(56) References Cited

U.S. PATENT DOCUMENTS

| | | | | |
|---|---|---|---|---|
| 5,810,881 A | * | 9/1998 | Hoskin | A61B 17/062 81/421 |
| 6,254,597 B1 | * | 7/2001 | Rizoiu | B23K 26/146 604/35 |
| 2005/0228441 A1 | * | 10/2005 | Wood | A61B 17/062 606/205 |
| 2007/0239202 A1 | | 10/2007 | Rodriguez | |
| 2011/0111247 A1 | | 5/2011 | Lemke et al. | |
| 2013/0014375 A1 | * | 1/2013 | Hempstead | A61B 18/1442 264/129 |
| 2014/0243850 A1 | | 8/2014 | Sadaka | |

FOREIGN PATENT DOCUMENTS

| | | |
|---|---|---|
| DE | 19733036 C1 | 6/1999 |
| DE | 202004008169 U1 | 7/2004 |
| DE | 102016110294 A1 | 12/2017 |

OTHER PUBLICATIONS

Search Report received in International Application No. PCT/EP2021/055357 dated May 18, 2021, with translation, 6 pages.

\* cited by examiner

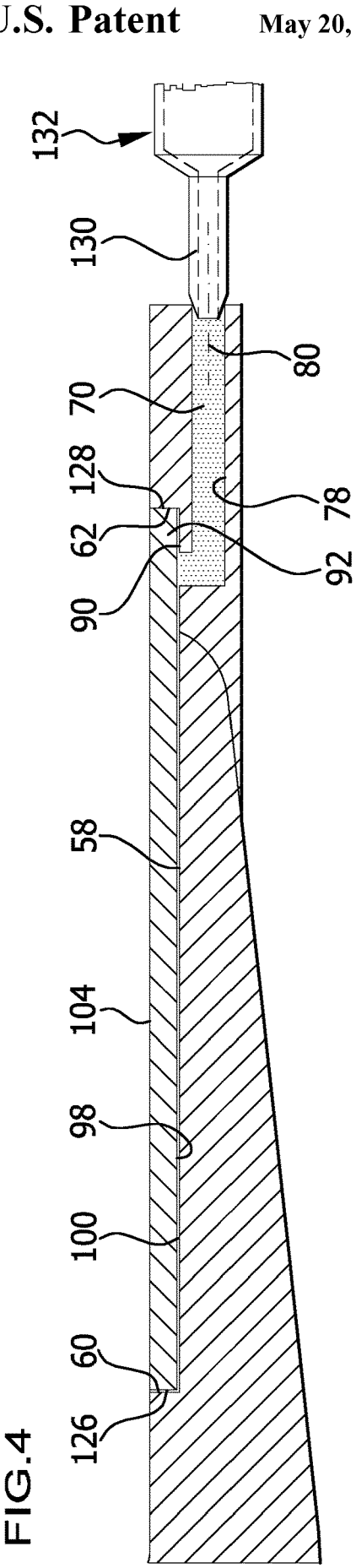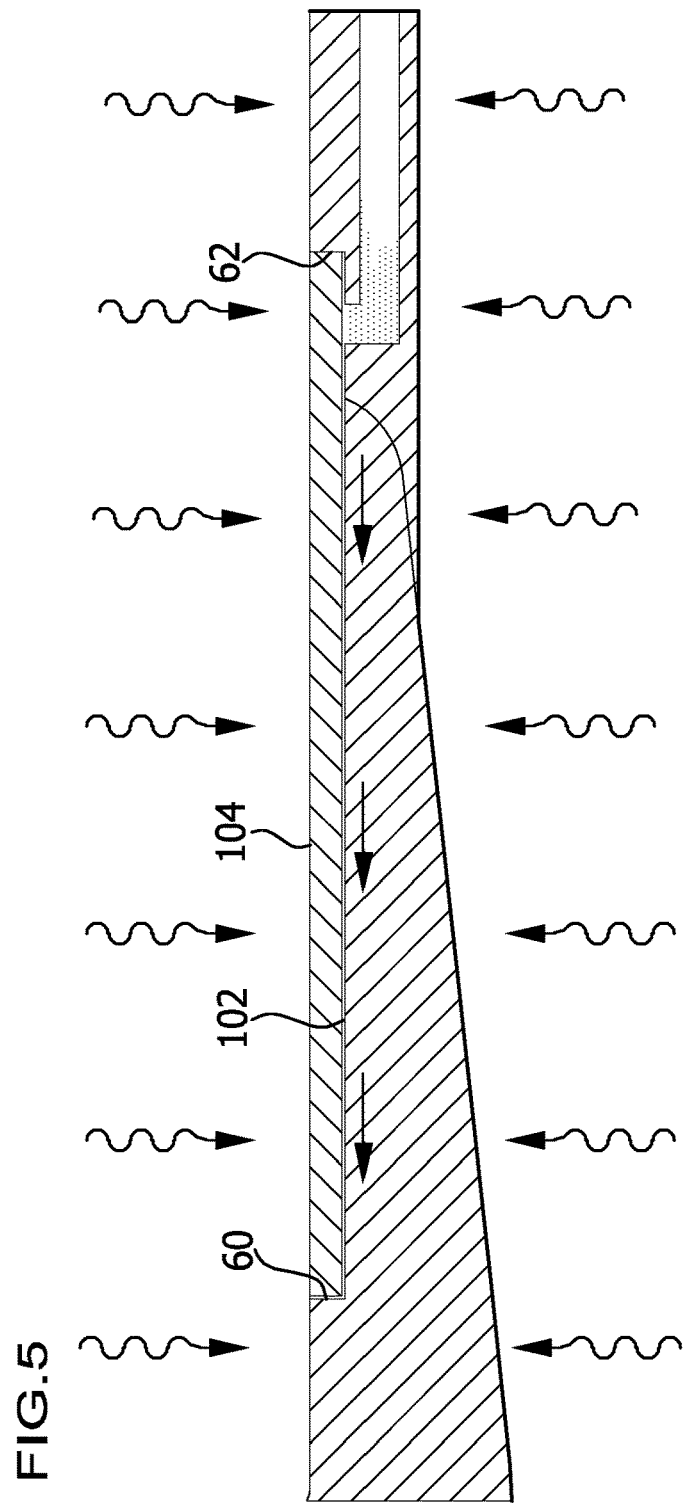

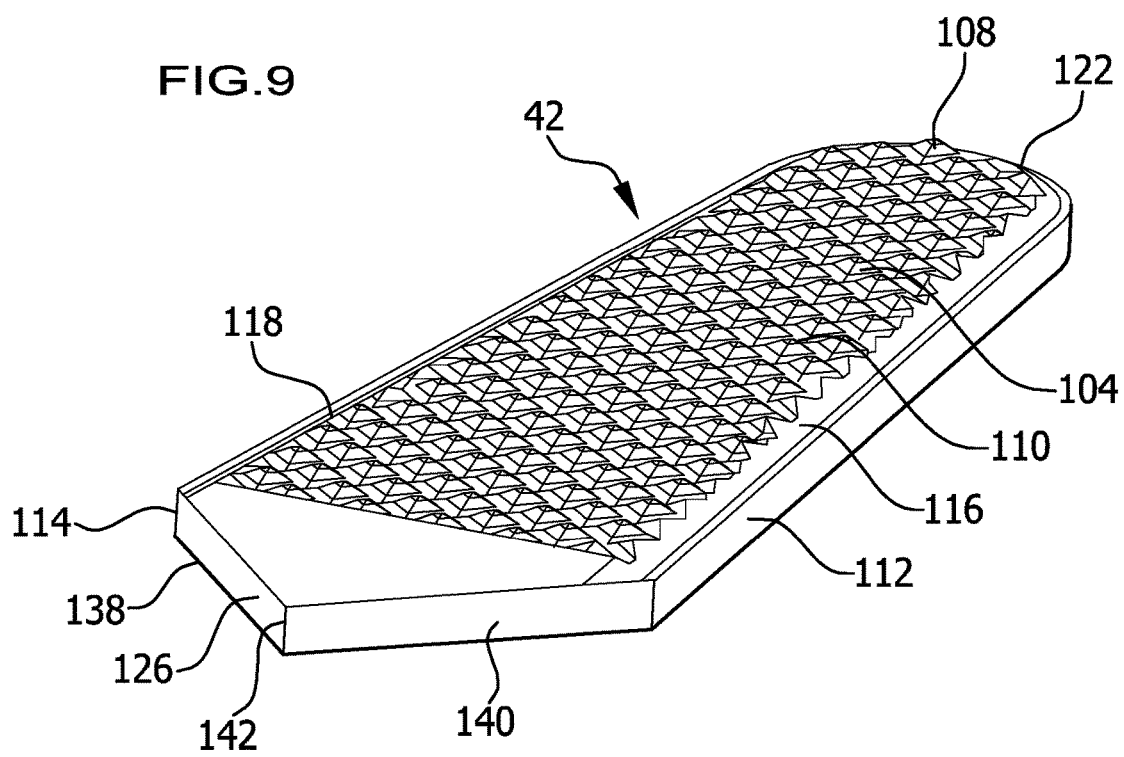
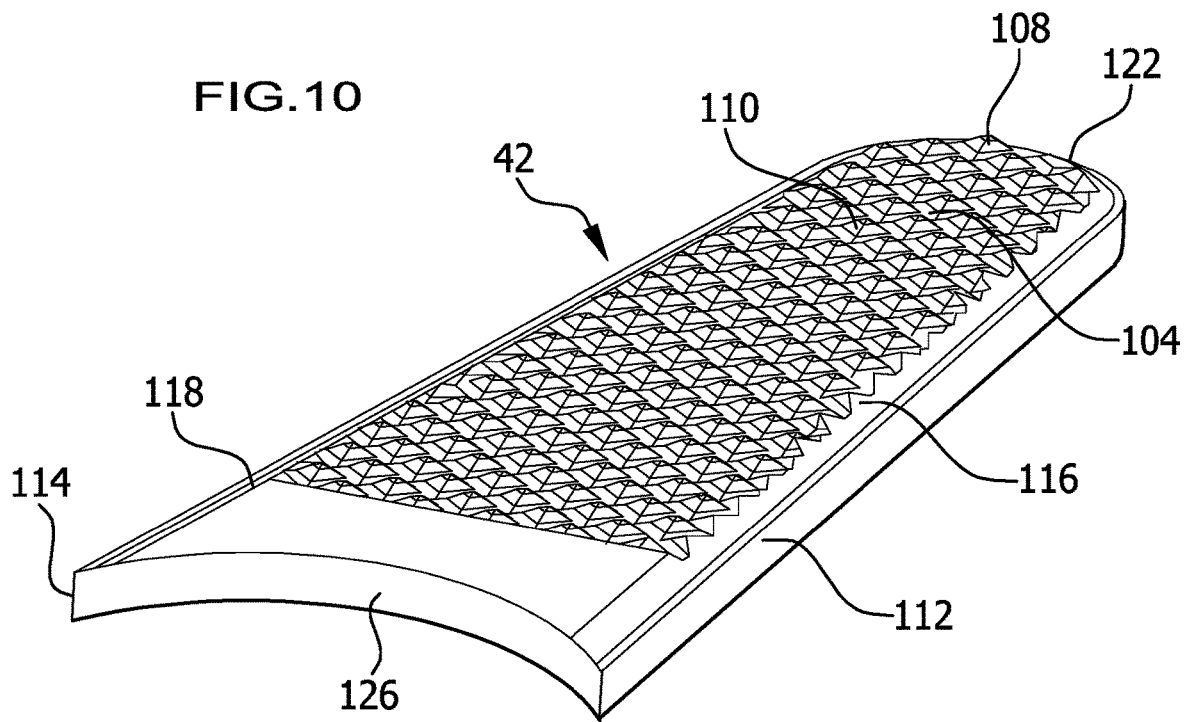

INSTRUMENT PRE-PRODUCT AND MEDICAL INSTRUMENT

CROSS-REFERENCE TO RELATED APPLICATIONS

This application is a continuation of international application number PCT/EP2021/055357 filed on Mar. 3, 2021 and claims priority to German application number 10 2020 105 886.1 filed on Mar. 5, 2020.

The present disclosure relates to the subject matter disclosed in international application number PCT/EP2021/055357 of Mar. 3, 2021 and German application number 10 2020 105 886.1 of Mar. 5, 2020, the contents of both applications being incorporated herein by reference in their entireties and for all purposes.

FIELD

The present disclosure relates to semi-finished instruments generally, and more specifically to a semi-finished instrument comprising an instrument body part blank for forming an instrument body part of a medical instrument, which instrument body part blank is made of a metal, in particular an instrument steel, a distal end region, and on the distal end region a recess for accommodating a hard metal element, wherein the recess has an abutment face for the hard metal element.

Furthermore, the disclosure relates to medical instruments generally, and more specifically to a medical instrument comprising at least one instrument body part.

BACKGROUND

"Semi-finished instruments", also called "instrument pre-products", and medical instruments of the kind described at the outset are known in a wide range of embodiments. For example, they are used as needle holders to grasp, hold, and guide surgical needles.

Needle holders typically comprise two instrument body parts in the form of branches, which are pivotably mounted against one another and which on their distal end are configured in the form of mouth parts. These form clamping jaws, between which a needle can be clampingly held.

It is particularly important for needle holders that a needle can be held between the mouth parts in an absolutely slip- and tilt-resistant manner. The surfaces of the clamping jaws are therefore typically of structured configuration. In order to keep wear to the structures of the clamping jaws, also referred to as profiles, as minimal as possible, it is common to use hard metal jaws in needle holders, which are configured in the form of hard metal platelets and are connected to the mouth parts in such a way that they form at least part of a surface of the side faces of the clamping jaws that face toward one another.

The hard metal platelets, which form hard metal inserts, can be jointed to the instrument body parts, which are made of a metal, for example by soldering, in particular by brazing. Relative movements when joining can often still occur despite correct positioning of the hard metal inserts at room temperature. In other words, in the worst case, it can lead to soldering between the hard metal insert and the instrument body part not in the original starting position before being placed in the hardening furnace, thereby leading to larger solder gaps in the transition region between the hard metal insert and the instrument body part. However, solder gaps of that kind have a negative influence on the quality of the solder connection. In particular, it may lead to defects, to cracking, or to brittle phases with lacking mechanical strength.

A further problem is, in particular, that the amount of solder present in the solder gap between the hard metal insert and the instrument body blank is not sufficient due to diffusion of solder both into the material from which the instrument body part blank is made and into the hard metal insert. This results in defects, cavities, and the formation of pores.

To circumvent the problems described, a generous excess of solder is typically applied from the outside. However, this requires that the hard metal inserts must be produced significantly oversized in relation to the final mouth shape of the instrument and must be soldered to the instrument body part blank. However, the oversized production requires that the hard metal inserts must be ground down to the desired dimensions, which is time- and cost-intensive.

After the connection between the hard metal insert and the instrument body part blank, both the excess solder and an overhang of the hard metal inserts have to be elaborately reworked by means of a manual grinding process. There is a risk of heating the material of which the instrument body part blank is made to too great of an extent, thereby increasing a susceptibility of the medical instrument to corrosion.

Furthermore, the excess of solder that is provided can lead to further problems. It is thus known that chromium is bound by solder because it has a high affinity to the typically used solder additives. It can therefore result in a chromium depletion in the diffusion zone of the material from which the instrument body part blank is made. In particular, this effect can occur in the case of martensitic stainless steel like, e.g., the material 1.4021. An undesired consequence of the chromium depletion is, in particular, that a subsequent action of aggressive cleaning agents by the user leads to a corrosion of the instrument in the region of the material of which the instrument body part blank is made. In addition, it must be prevented that the excess solder spreads in gaps and surfaces, which during the soldering process, in the worst case, can lead to the two mouth parts of the instrument being soldered together if they are held against one another in the hardening furnace. To prevent this, before soldering, those parts that may come into contact with the solder during hardening must be completely coated with a material referred to as a solder stop, which prevents the penetration of solder.

As described, the known process for connecting the hard metal inserts to the instrument body part blanks, i.e. the entire soldering process, is very labor intensive and thus costly. This is one reason why the process comprises many, partially manual work steps and thus has only a low process security.

SUMMARY

In a first aspect of the disclosure, a semi-finished instrument comprises an instrument body part blank for forming an instrument body part of a medical instrument. Said instrument body part blank is made of a metal, in particular an instrument steel. The semi-finished instrument comprises a distal end region, and a recess on the distal end region for accommodating a hard metal element. The recess has an abutment face for the hard metal element. The instrument body part blank comprises a solder chamber for accommodating solder. The solder chamber is fluidically connected to the recess.

In a second aspect of the disclosure, a medical instrument, in particular in the form of a needle holder, comprises at least one instrument body part. The at least one instrument body part is made from a semi-finished instrument. The semi-finished instrument comprises an instrument body part blank for forming an instrument body part of a medical instrument. Said instrument body part blank is made of a metal, in particular an instrument steel. The semi-finished instrument comprises a distal end region, and a recess on the distal end region for accommodating a hard metal element. The recess has an abutment face for the hard metal element. The instrument body part blank comprises a solder chamber for accommodating solder. The solder chamber is fluidically connected to the recess.

BRIEF DESCRIPTION OF THE DRAWING FIGURES

Figure 2:
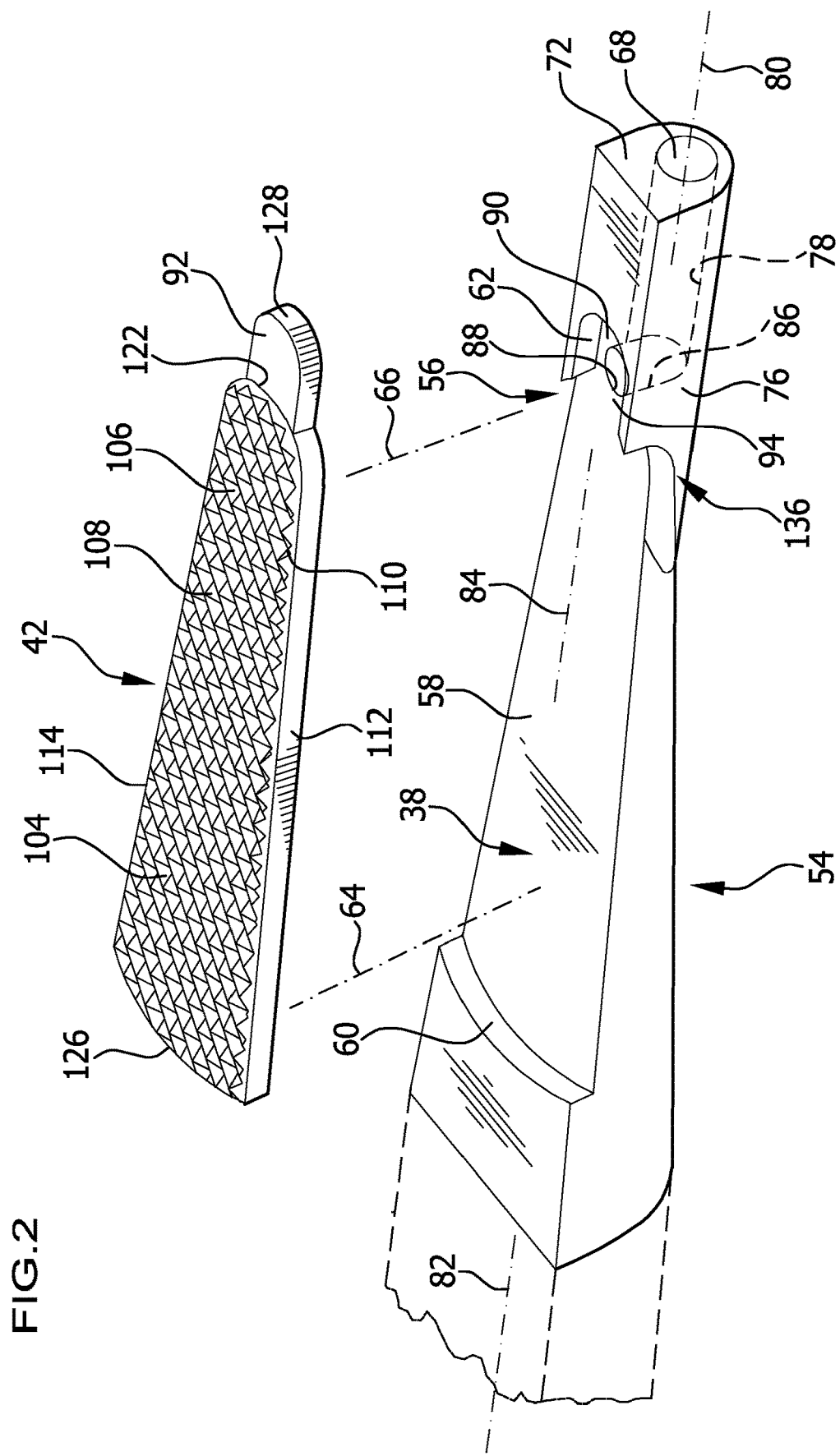
Figure 3:
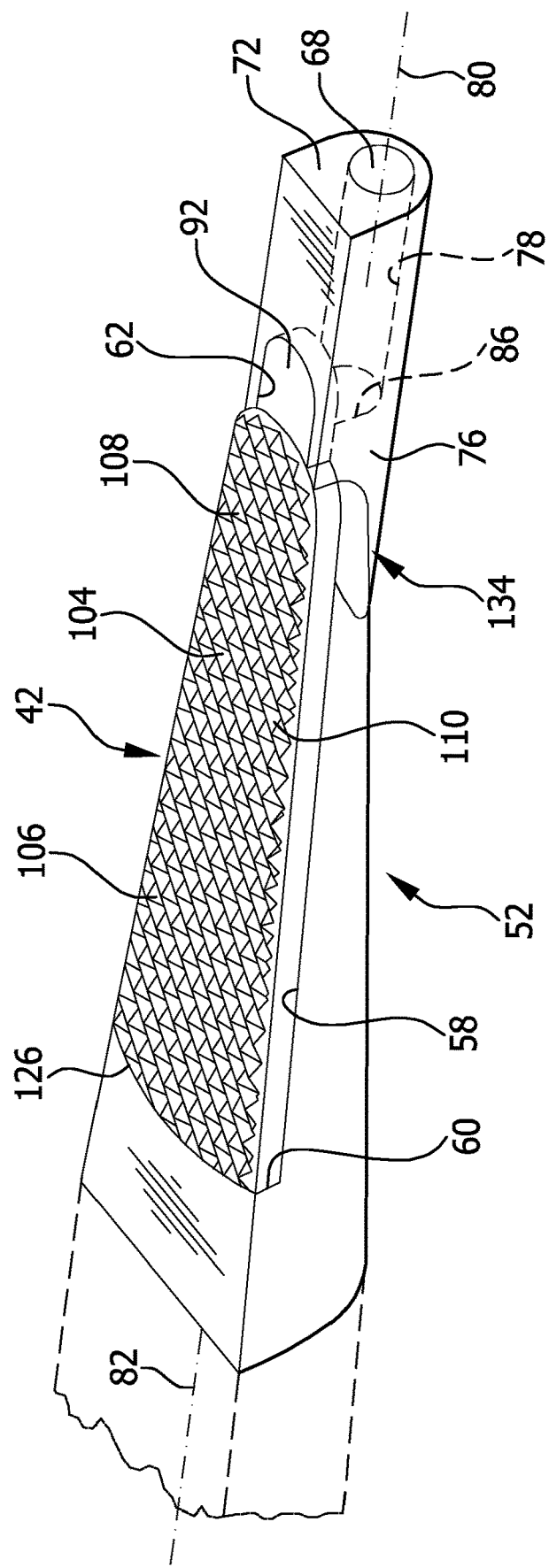
Figure 6:
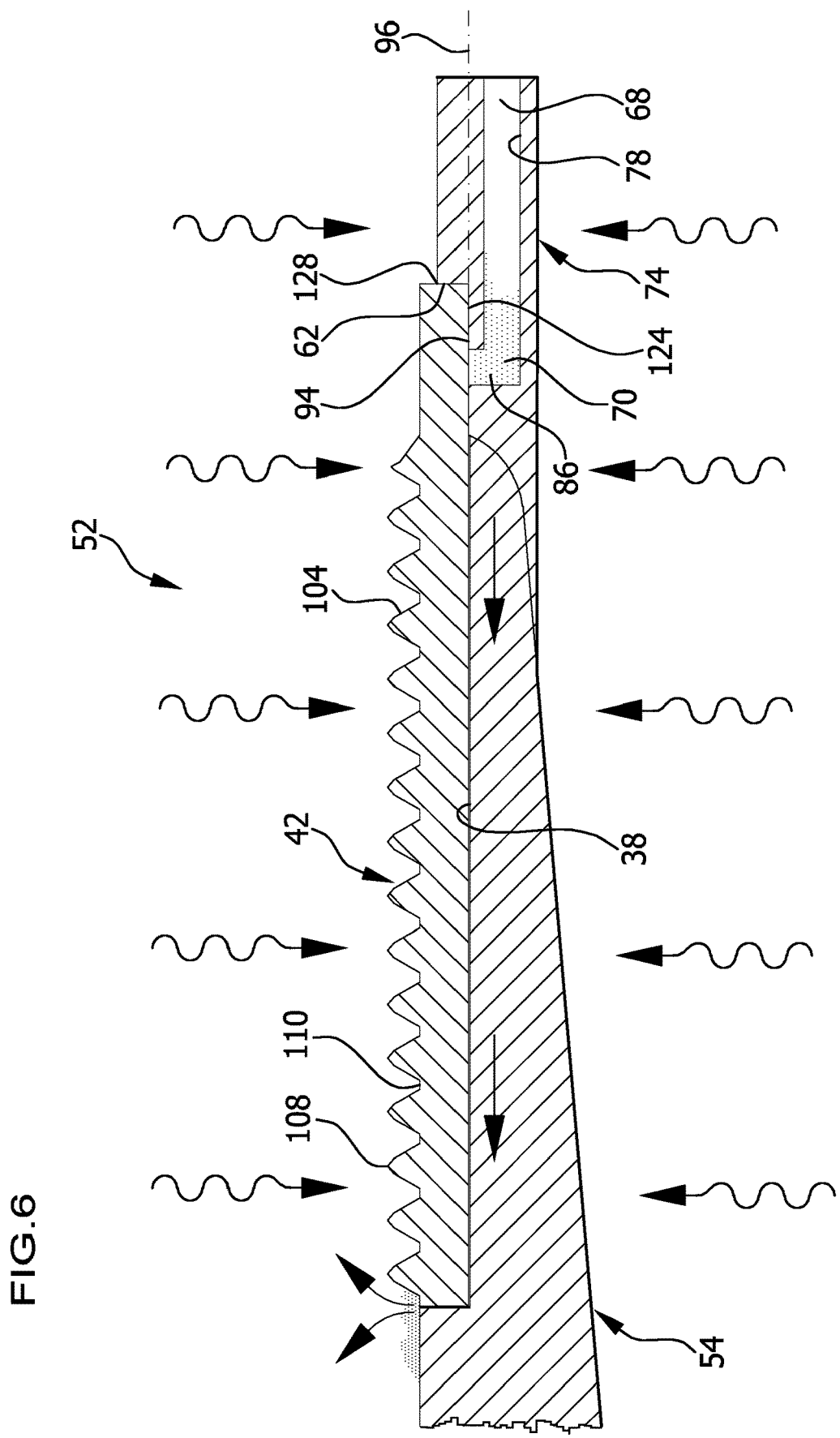
Figure 7:
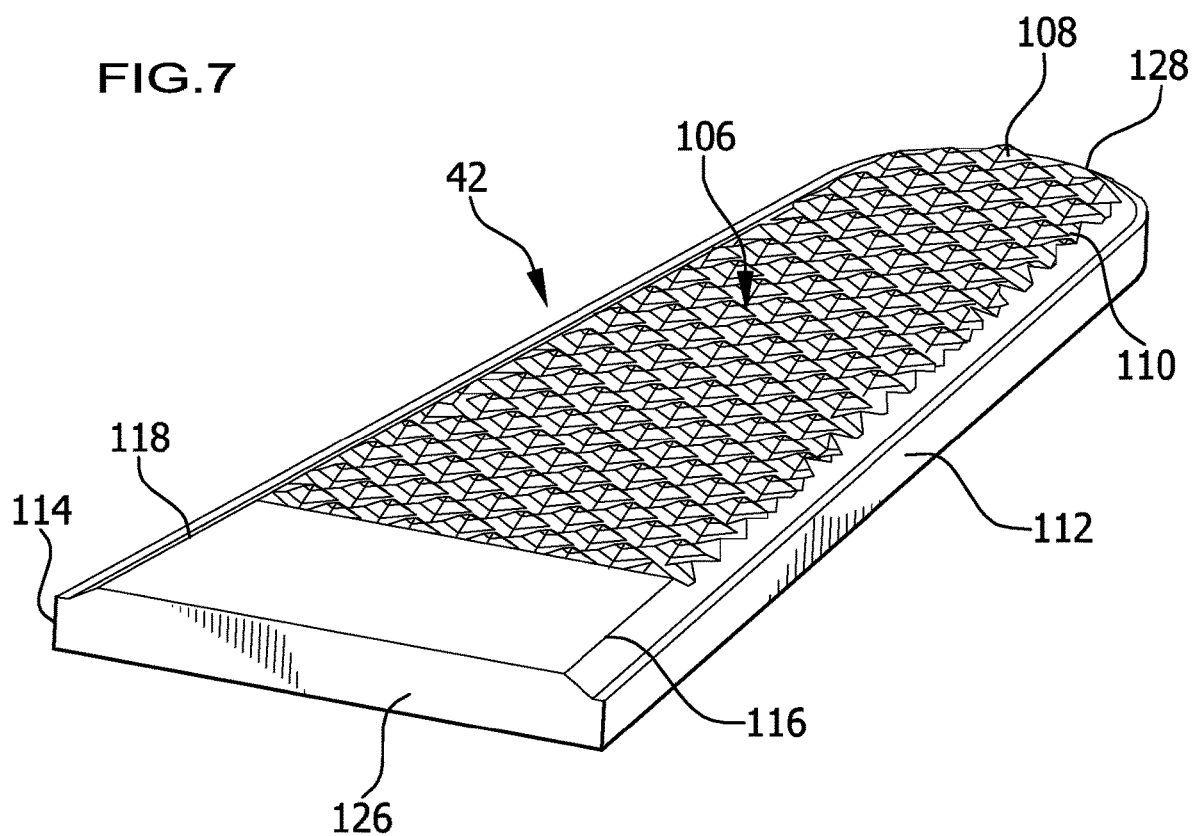
Figure 8:
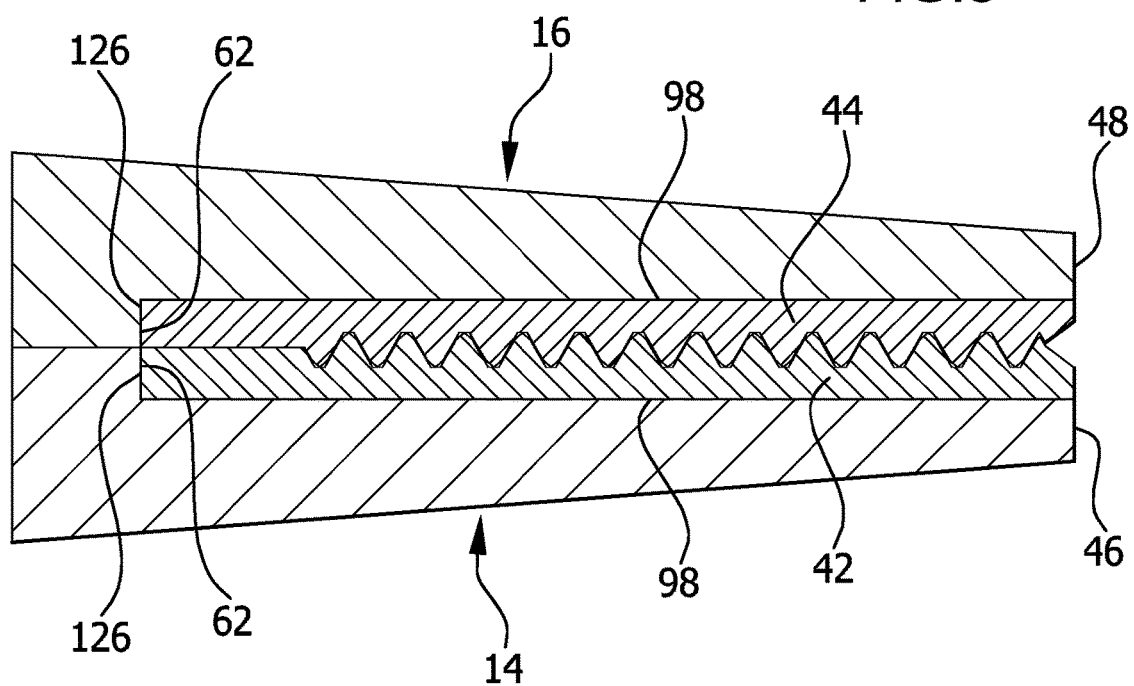
Figure 11:
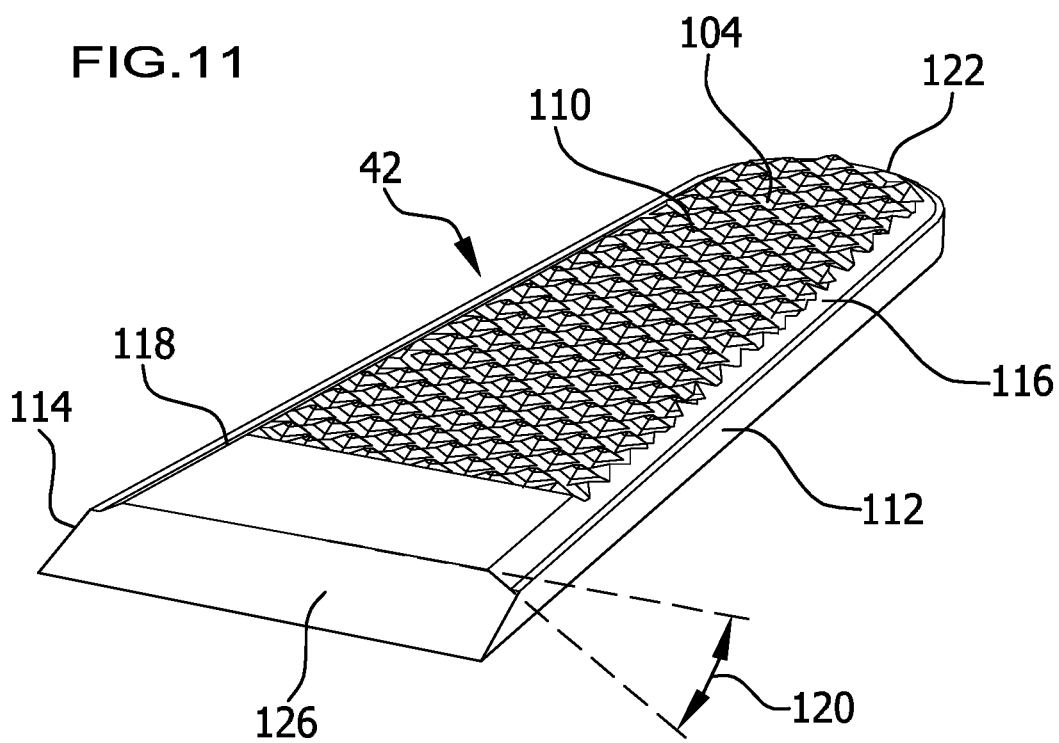
Figure 12:
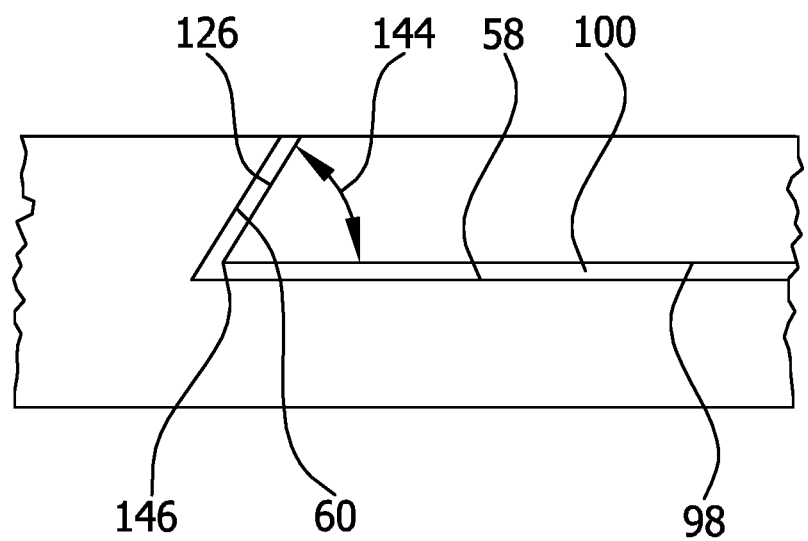

The foregoing summary and the following description may be better understood in conjunction with the drawing figures, of which:

FIG. 1: shows a perspective schematic total view of an embodiment of a medical instrument;

FIG. 2: shows a schematic perspective partial view of an instrument body part blank before the insertion of a hard metal element into a receptacle on the instrument body part blank;

FIG. 3: shows a view similar to FIG. 2, but with a hard metal element inserted into the recess on the instrument body part blank;

FIG. 4: shows a schematic longitudinal cut view of an embodiment of an instrument body part blank with an inserted hard metal element during the filling of the solder chamber with solder;

FIG. 5: shows a schematic view of the arrangement from FIG. 4 during the soldering of the instrument body part blank and the hard metal element;

FIG. 6: shows a schematic cut view similar to FIG. 4 of a further embodiment;

FIG. 7: shows a schematic perspective view of an embodiment of a hard metal element;

FIG. 8: shows a schematic cut view of a distal end region of an embodiment of a medical instrument;

FIG. 9: shows a schematic perspective view of a further embodiment of a hard metal element;

FIG. 10: shows a schematic perspective view of a further embodiment of a hard metal element;

FIG. 11: shows a schematic perspective view of a further embodiment of a hard metal element; and FIG. 12: shows a cut view similar to FIG. 4 of a further embodiment with a recess on the instrument body part blank that is undercut on one side.

DETAILED DESCRIPTION

Although the disclosure is illustrated and described herein with reference to specific embodiments, the disclosure is not intended to be limited to the details shown. Rather, various modifications may be made in the details without departing from the disclosure.

The present disclosure relates to semi-finished instrument comprising:
an instrument body part blank for forming an instrument body part of a medical instrument, said instrument body part blank being made of a metal, in particular an instrument steel,
a distal end region, and
a recess on the distal end region for accommodating a hard metal element,
wherein:
the recess has an abutment face for the hard metal element,
the instrument body part blank comprises a solder chamber for accommodating solder, and
the solder chamber is fluidically connected to the recess.

The solution proposed in accordance with the disclosure makes it possible, in particular, to exactly predetermine an amount of solder. This is achieved, in particular, by the shape and size of the solder chamber being predetermined. When the solder chamber is completely filled with solder, the amount of solder is exactly predetermined. As a result of the fluidic connection of the solder chamber to the recess that accommodates the hard metal element, the solder, when hardening, can be drawn out of the solder chamber by capillary action into the solder gap between the hard metal element and the abutment face. When there is no more capillary action, the solder can no longer flow. The problems described above that result due to a large excess of solder that is currently used and due to an uncontrolled flow of solder can thus be prevented. Because of the ability to exactly dose the solder by predetermining the solder chamber, namely the volume thereof, the coating of the instrument body part blank with solder stop and the typical generous overhang of the hard metal inserts over the instrument body part blank can be forgone. The subsequent expenditure that is required for processing the semi-finished instrument, in particular by grinding, is thereby significantly reduced. In addition, the provision of the solder chamber, which may be arranged or formed, in particular, on the instrument body part blank in such a way that it can be removed therefrom after the soldering of the hard metal insert in the recess of the instrument body part blank, has the advantage that the hard metal insert can be soldered to the instrument body part blank in its final or substantially final form. For example, the hard metal insert may be configured in the form of a hard metal platelet, which is already structured in the desired way, i.e., having a structured or profiled surface that is optimal for holding a needle, and otherwise defines a desired shape, for example with lateral chamfers. A further processing expenditure for forming the semi-finished instrument can thereby be largely minimized. The described further development is advantageous, in particular, if hard metal platelets forming hard metal inserts are connected by means of a vacuum high-temperature soldering process to the instrument body parts that are made of a metal. Large temperature differences during the hardening process, which is performed at about 1000° C., and different thermal expansion coefficients of the instrument body part and the hard metal insert then no longer lead to the undesired formation of defects, cracks, or brittle phases with lacking mechanical strength.

The semi-finished instrument favorably comprises a hard metal element. The hard metal element may be, e.g., of platelet-shaped configuration and have a structured or profiled surface. In particular, the hard metal element may already have its final form, so that it does not have to be processed further, in particular by grinding, after being connected to the instrument body part blank.

It is favorable if the hard metal element is of platelet-shaped configuration. Such a hard metal element can be handled in a simple manner and can be securely connected to the instrument body part blank in the described manner by soldering.

The hard metal element preferably has a soldering face for placing against the abutment face. When connecting the hard metal element to the instrument body part blank, a solder gap forms between the soldering face and the abutment face, into which gap the solder is drawn out of the solder chamber by capillary action.

It is favorable if the hard metal element is inserted into the recess and connected to the instrument body part blank by soldering. A permanent and reliable connection between the hard metal insert and the instrument body part blank can be achieved in this way.

An optimal connection between the hard metal insert and the instrument body part blank can be achieved, in particular, by a solder layer being formed between the abutment face and the soldering face. Said solder layer is preferably continuous and not interrupted, so that the abutment face and the soldering face are completely separated from one another by the solder layer. A thickness of the solder layer may be, in particular, less than 0.05 mm.

In accordance with a further embodiment, provision may be made that the hard metal element has a tool side face and that the tool side face and the soldering face point in opposite directions. In particular a flat hard metal platelet can thus be formed, which forms the hard metal element. The tool side face, for example a profiled or structured surface of the hard metal element for grasping and holding a needle, can then be provided already in a desired form before being connected to the instrument body part blank.

Depending on the kind of element to be formed, it is favorable if the tool side face is of planar or substantially planar configuration or is structured. In particular, the tool side face may be provided with a macroscopic structure. In the present case, macroscopic means that depressions or projections of the tool side face are greater than about 0.1 millimeter.

The configuration of the semi-finished instrument can be simplified, in particular, by the tool side face having a regular structure. In addition, a needle can thus be held in a defined manner with an instrument, for example a needle holder.

It is advantageous if the structure has a plurality of projections and depressions formed between them. This makes it possible, in particular, for example to securely hold a needle between two clamping jaws of a medical instrument. In particular, the projections can partially dig into the needle and the depressions can partially accommodate the needle.

A good holding effect can be achieved, in particular, by the projections being of pyramidal configuration. In particular, they may be configured in the form of a three- or four-sided pyramid.

Further, it is favorable if the hard metal element has at least one side edge extending transversely to the tool side face and if a chamfer is formed in the transition region of the tool side face and the at least one side edge. In particular, the chamfer may be formed at angle in a range from about 35° to about 55°. As already explained at the outset, the processing of the hard metal insert after the connection to the instrument body part blank is associated with the risk of the instrument later having an increased susceptibility to corrosion. The described configuration of the instrument body part blank thus has the advantage of being able to provide the hard metal insert already in its final form because of the predetermined, defined amount of solder due to the defined solder chamber. A subsequent chamfering of the hard metal insert to avoid sharp edges, as is necessary or is performed with the conventional configuration of medical instruments, is unnecessary with a hard metal element that is already correspondingly configured.

It is advantageous if two chamfers that extend in parallel or substantially in parallel to one another or extend toward one another in the direction toward a distal end are formed on the hard metal element. A hard metal element formed in that way makes it possible, in particular, to be connected to a recess on the instrument body part blank that tapers in the distal direction. Mouth parts that taper in the distal direction can thereby be formed on medical instruments in a simple manner.

The instrument body blank can be produced in a simple manner if the solder chamber comprises a bore or is configured in the form of a bore. A volume of the solder chamber can thus be predetermined in a simple manner, namely by the length and diameter of the bore.

In accordance with a further embodiment, provision may be made that the solder chamber defines a solder chamber longitudinal axis, that the recess defines a recess longitudinal axis, and that the solder chamber longitudinal axis and the recess longitudinal axis extend in parallel or substantially in parallel to one another. A configuration of that kind enables, in particular, a simple handling of the instrument body part blank. In addition, the solder chamber can thus be filled with solder in a simple manner before soldering the hard metal insert to the instrument body part blank. In particular, this becomes particularly simple if the solder chamber is formed on a projection of the instrument body part blank that extends, e.g., in the distal direction away from the recess for accommodating the hard metal insert.

In order to be able to ensure a flow of solder in the desired manner from the solder chamber between the abutment face and the soldering face, i.e., into the solder gap, it is advantageous if the solder chamber is fluidically connected to the recess by way of a transverse connection that extends transversely, in particular perpendicularly, to the solder chamber longitudinal axis.

The semi-finished instrument can be formed in a simple manner if the transverse connection is configured in the form of a transverse bore.

In order to enable the flow of solder between the soldering face and the abutment face in as unhindered a manner as possible, it is favorable if the transverse connection passes through the abutment face. The solder can then flow from the solder chamber through the transverse connection and directly into the solder gap.

The handling of the instrument body part blank and the configuration of the semi-finished instrument are further simplified, in particular, by the solder chamber being arranged or formed on a distal end of the instrument body part blank. The solder chamber can thus be filled with solder in a simple manner. Further, with a corresponding configuration, it can optionally be removed in a simple manner after the connection of the hard metal insert to the instrument body part blank.

In accordance with a further embodiment, provision may be made that the instrument body part blank comprises a solder chamber portion, that the solder chamber is arranged or formed on the solder chamber portion, and that the solder chamber portion is configured so as to be separable from the instrument body part blank. The solder chamber portion is thus only temporarily part of the instrument body part blank. Thus, in particular, it can be removed after the hard metal insert is soldered to the instrument body part blank. This is effected by separating the solder chamber portion from the remaining instrument body part blank. The solder chamber portion can thus initially be formed in one piece with the instrument body part blank and form part thereof, the role of which, in particular, is to accommodate solder in the solder chamber arranged or formed in the solder chamber portion for the soldering of the hard metal insert and the instrument body part blank. After soldering, the solder chamber is empty and is no longer needed. It can then be separated off, for example by sawing, grinding, or milling. This is possible in a simple manner if a bottleneck or constriction, for example a predetermined breaking point, is formed between the solder chamber portion and the remaining instrument body part blank.

It is favorable if the recess has a first end face and a second end face, if the first end face extends transversely to the abutment face, if the second end face extends transversely to the abutment face, and if the first end face and the second end face point toward one another or substantially toward one another. A recess configured in that way makes it possible, in particular, to delimit a movement of the hard metal element that is accommodated in the recess before forming the soldering connection, namely a movement between the first end face and the second end face.

In order to enable the insertion of the hard metal element into the recess in a defined manner, such that the hard metal element can be positioned in the recess in a desired manner, namely without further auxiliary means, it is advantageous if the first end face or the second end face together with the abutment face define an undercut. In particular, a distance of the hard metal element from the abutment face and thus a width of the solder gap can thus be predetermined in a simple and reproducible manner.

It is favorable if a contour of the first end face and a contour of the second end face differ from one another. This makes it possible, in particular, to configure the recess in such a way that an unambiguous position of the hard metal element in the recess is predetermined. Thus, the hard metal element can be positioned on the instrument body part blank in a defined manner. Depending on a remaining play, it can thus be ensured, in particular, that a preformed hard metal element is able to be used in the desired manner without it have to still be elaborately processed after being soldered to the instrument body part blank.

It is advantageous if the first end face and/or the second end face are of planar or substantially planar configuration or are formed concavely curved facing toward one another. In particular, the first end face and/or the second end face may be of concavely curved configuration with respect to an axis of curvature extending transversely to the abutment face. In addition, the first end face and the second end face may be of different configuration, so that the hard metal element is able to be accommodated in the recess in a positive-locking or substantially positive-locking manner, aside from a play that may possibly remain. Curvatures of the first end face and the second end face, in particular, may differ from one another in order to be able to predetermine a defined positioning of the hard metal element in the recess.

It is advantageous if a coupling receptacle is formed on the instrument body part blank for accommodating, in particular for accommodating in a positive-locking manner, a coupling projection that projects from the hard metal element and in particular is formed corresponding to the coupling receptacle. In particular the coupling receptacle in cooperation with the coupling projection on the hard metal element thus makes it possible to unambiguously position the hard metal element in the recess. In particular, a movement of the hard metal element relative to the instrument body part blank in a plane parallel to the abutment face or parallel to the soldering face can be effectively prevented. In particular, an at least partially positive-locking coupling between the instrument body part blank and the hard metal element can be achieved through the cooperation of the coupling receptacle and the coupling projection.

It is favorable if the coupling receptacle is arranged or formed on the solder chamber portion. This makes it possible, in particular, to separate off the coupling receptacle together with the solder chamber portion after the hard metal element is soldered to the instrument body part blank.

It is advantageous if the hard metal element comprises a projecting coupling projection and if the coupling projection is configured to be separable from the hard metal element. This configuration makes it possible, in particular, to separate off the coupling projection after soldering the hard metal element to the instrument body part blank, such that only the hard metal element, in particular with its tool side face, remains on the instrument body part blank for forming the semi-finished instrument.

In order to facilitate the separation of the coupling projection from the hard metal element, it is favorable if a thickness, in particular an average thickness, of the hard metal element is smaller in the region of the coupling projection than in the region of the tool side face.

In accordance with a further embodiment, provision may be made that the coupling receptacle has a coupling receptacle abutment face and that the coupling projection has a coupling projection soldering face for placing against the coupling receptacle abutment face. This configuration makes it possible, in particular, to connect the hard metal element and the instrument body part blank to one another by soldering, even in the region of the coupling receptacle and the coupling projection. Optionally, a distance between the coupling receptacle abutment face and the coupling projection soldering face may also be selected such that no capillary action occurs that draws solder between these two faces.

The coupling receptacle abutment face and the abutment face preferably define a common abutment plane. Such a configuration makes it possible to form the instrument body part blank in a simple manner.

In particular, in order to improve a stability of the semi-finished instrument, it is favorable if the transverse connection passes through the coupling receptacle abutment face. When the solder chamber portion is removed after connecting the hard metal element to the instrument body part blank, the removal of the transverse connection is also made possible with this configuration. In particular, it can thus be prevented that cavities remain on the semi-finished instrument after the soldering of the hard metal element and the instrument body part blank, which can have a negative effect on the stability of the instrument.

Further, it may be favorable if the instrument body part blank comprises a predetermined breaking point and if the predetermined breaking point is arranged or formed for the separation of the solder chamber, in particular the solder chamber portion, from the instrument body part blank. Such a predetermined breaking point facilitates, in particular, the separation of the solder chamber, in particular together with the solder chamber portion, from the instrument body part blank. Thus, that part of the instrument body part blank that is only needed for defining an amount of solder for connecting the hard metal element and the instrument body part blank can be removed in a simple and secure manner after the soldering of the hard metal element and the instrument body part blank.

The predetermined breaking point can be formed in a simple manner if it is configured in the form of a weakened region between a distal end of the instrument body part and the solder chamber portion.

It is favorable if the instrument body part blank is formed by cold- or hot-forming. Instrument body part blanks of that kind can be formed in a simple and defined manner.

Further, the disclosure relates to a medical instrument, in particular in the form of a needle holder, comprising at least one instrument body part, wherein the at least one instrument body part is made from a semi-finished instrument, said semi-finished instrument comprising an instrument body part blank for forming an instrument body part of a medical instrument, said instrument body part blank being made of a metal, in particular an instrument steel, a distal end region, and a recess on the distal end region for accommodating a hard metal element, wherein the recess has an abutment face for the hard metal element, wherein the instrument body part blank comprises a solder chamber for accommodating solder and wherein the solder chamber is fluidically connected to the recess.

Such a medical instrument can be formed in an advantageous manner as described above. In addition, unlike conventional medical instruments in which metal inserts are soldered to an instrument body part blank, it is significantly less susceptible to corrosion.

It is advantageous if the hard metal element and the instrument body part are connected to one another by soldering, if the solder chamber, in particular the solder chamber portion, is separated off, and if a distal end of the at least one instrument body part is processed by grinding, milling, or polishing. As described above, it is possible, in particular, to provide the hard metal element practically in its final form to be soldered to the instrument body part blank. This is possible, in particular, due to the fact that, as a result of the solder chamber, exactly the amount of solder required is provided that is necessary for soldering the hard metal element and the instrument body part blank to one another. In a preferred embodiment of the medical instrument, the processing of the instrument body part by means of grinding, milling, or polishing is only necessary in the region where a solder chamber portion was provided, namely in order to separate off said solder chamber portion. Such processing is visible and detectable on a finished medical instrument.

It is advantageous if the medical instrument comprises two instrument body parts in the form of branches that are movably coupled to one another. For example, they may be displaceably mounted against one another. Alternatively, for example, they may also be mounted against one another so as to be pivotable about a common pivot axis. Thus, a wide variety of instruments can be formed, for example clamps or needle holders.

The production of the medical instrument is further simplified, in particular, by the fact that the hard metal elements of the two instrument body parts are of identical configuration.

It is advantageous if the tool side faces of the two identical hard metal elements each have a macroscopic structure, in each case with a plurality of projections and depressions formed therebetween, if the projections of the one hard metal element in a maximally proximate position of the two hard metal elements engage into the depressions of the respective other hard metal element, and if outer contours of the two hard metal elements in the maximally proximate position cover one another congruently or substantially congruently. The projections and depressions, which can also be referred to as tooth tips and tooth roots, can thus interengage with one another in the maximally proximate position, in particular a closed position of the instrument. Due to the particular arrangement of the regular structure of projections and depressions, unlike is known from the prior art, there is no lateral offset of the two cooperating hard metal elements, instead they are able to cover one another congruently in the maximally proximate position. The macroscopic structure of the two hard metal elements may, in particular, be of regular configuration.

Two instrument body parts can be coupled to one another in a simple manner with a connecting screw or by riveting, pressing, or welding a joint pin. The connecting screw, a rivet, or the joint pin thus can define, in particular, a pivot axis and also predetermine a play of the two instrument body parts relative to one another.

It is favorable if the medical instrument is configured in the form of a needle holder. Surgical needles can be securely grasped, held, and handled with such a needle holder. In addition, such needle holders are less susceptible to corrosion in comparison to needle holders known from the prior art.

A first embodiment of a medical instrument 10 is schematically depicted in FIG. 1 and is denoted as a whole with the reference numeral 10. The instrument 10 is configured in the form of a needle holder 12.

The instrument 10 comprises two instrument body parts 14 and 16 that are movably coupled to one another. In the embodiment the instrument body parts 14 and 16 are connected to one another with a connecting screw 18 in the known manner. The connecting screw 18 defines a pivot axis 20 about which the instrument body parts 14 and 16 are pivotable relative to one another.

The instrument body parts 14 and 16 are configured in the form of branches 22 and 24, on the proximal ends of which a respective finger ring 26 and 28 is arranged.

Arranged between proximal ends of the branches 22 and 24 is a locking device 30 for blocking a movement of the proximal ends of the instrument body parts 14 and 16 away from one another. The locking device 30 is configured such that a locking can be achieved for different spacings of the proximal ends of the branches 22 and 24.

The instrument body parts 14 and 16 are connected to one another in a connecting region 32 by the connecting screw 18. The connecting region 32 is configured in the form of a push-through connection.

The instrument body parts 14 and 16 form mouth parts 34 and 36 on the distal side of the connecting region 32.

The mouth parts 34 and 36 each have a recess 38 and 40, which accommodates a respective hard metal element 42 and 44. The hard metal elements 42 and 44 are connected to the respective instrument body part 14 and 16 by soldering.

Distal ends 46 and 48 of the instrument body parts 14 and 16 are processed by grinding and/or polishing.

By means of the needle holder 12, needles 50, as is schematically depicted in FIG. 1, can be grasped, held, and guided for forming stitches.

The recesses 38 and 40 are arranged and formed in such a way that they face toward one another in the finished instrument 10. In other words, the hard metal elements 42 and 44 face toward one another and abut against one another in a closed position when the instrument 10 is closed, i.e. when the mouth parts 34 and 36 are moved toward one another to a maximum extent. The needles 50 can then be held between the hard metal elements 42 and 44.

The instrument body parts 14 and 16 are each made from a semi-finished instrument 52. The structure and the production of a semi-finished instrument 52 are explained in more detail in the following with reference to FIGS. 2 to 12.

Depicted as an example in FIG. 2 is a distal end region 56 of a instrument body part blank 54. The instrument body part blank 54 is made of a metal. In one embodiment, the metal is an instrument steel.

The recess 38 is formed on the distal end region 56 of the instrument body part blank 54. A semi-finished instrument 52 is made from the instrument body part blank 54, which after completion forms the instrument body part 14.

The recess 38 serves to accommodate the hard metal element 42 and defines an abutment face 58 for the hard metal element 42. The abutment face 58 is planar in the embodiment.

The recess 38 has a first end face 60 and a second end face 62. The first end face 60 extends transversely to the abutment face 58. The second end face 62 also extends transversely to the abutment face 58. Further, the first end face 60 and the second end face 62 point toward one another or substantially toward one another.

Contours of the first end face 60 and the second end face 62 differ from one another in the embodiment of the instrument body part blank 54 depicted in FIG. 2. Further, in the embodiment of the instrument body part blank 54 depicted in FIG. 2, both the first end face 60 and the second end face 62 are formed concavely curved facing toward one another, namely in relation to a respective first axis of curvature 64 and second axis of curvature 66 extending transversely, in particular perpendicularly, to the abutment face 58.

The instrument body part blank 54 further comprises a solder chamber 68 for accommodating solder 70.

The solder chamber 68 is arranged or formed on a distal end 72 of the instrument body part blank 54.

The instrument body part blank 54 comprises a solder chamber portion 74, on which the solder chamber 68 is arranged or formed.

The solder chamber portion 74 is of separable configuration and can be removed, as described in the following, from the instrument body part blank 54 after soldering the hard metal element 42 to the instrument body part blank 54.

The solder chamber portion 74 is configured in the form of a substantially cuboidal body 76 that extends the distal end region 56 of the instrument body part blank 54. The solder chamber 68 is configured in the form of a bore 78, the solder chamber longitudinal axis 80 of which extends in parallel or substantially in parallel to a longitudinal axis 82 of the instrument body part blank 54 in the region of the distal end region 56. The longitudinal axis 82 extends in parallel to a recess longitudinal axis defined by the recess 38, so that the solder chamber longitudinal axis 80 and the recess longitudinal axis 84 extend in parallel or substantially in parallel to one another.

The solder chamber 68 is fluidically connected to the recess 38. This is achieved by way of a transverse connection 86 that extends transversely, namely perpendicularly in the embodiment depicted in FIG. 2, to the solder chamber longitudinal axis.

The transverse connection 86 is configured in the form of a transverse bore 88. The transverse connection 86 also passes through the abutment face 58.

In the embodiment of the instrument body part blank 54 depicted in FIG. 2, a coupling receptacle 90 is also formed for accommodating a coupling projection 92, which is formed projecting from the hard metal element 42.

The coupling receptacle 90 is arranged or formed on the solder chamber portion 74. It has a coupling receptacle abutment face 94, which together with the abutment face 58 defines a common abutment plane 96.

In the embodiment of the instrument body part blank 54 depicted in FIGS. 2 to 4, the transverse connection 86 passes through the coupling receptacle abutment face 94.

In the embodiment of the hard metal element 42 depicted in FIGS. 2 to 4, the coupling projection 92 is configured corresponding to the coupling receptacle 90, so that the coupling projection 92 is accommodated in the coupling receptacle 90 in a positive-locking or substantially positive-locking manner when the hard metal element 42 is inserted into the recess 38, as can be seen in FIG. 3, for example.

The hard metal element 42 is of platelet-shaped configuration and has a soldering face 98 for placing against the abutment face 58.

However, for soldering the hard metal element 42 to the instrument body part blank 54, a narrow solder gap 100 is formed between the abutment face 58 and the solder face 98. A width of the solder gap 100 is at most about 0.05 mm in order to be able to generate a capillary action for the solder 70. After soldering the hard metal element 42 and the instrument body part blank 54, a thin layer of solder 102 is formed between the abutment face 58 and the soldering face 98, the thickness of which corresponds to about a width of the solder gap 100.

The hard metal element 42 also has a tool side face 104, the tool side face 104 and the soldering face 98 pointing in opposite directions.

In the embodiment of the hard metal element 42 depicted in FIGS. 2 and 3, the tool side face 104 is of structured configuration and has a macroscopic structure 106. The structure 106 of the tool side face 104 is of regular configuration. The structure 106 has a plurality of projections 108 and depressions 110 formed therebetween.

In one embodiment, the projections 108 are of pyramidal configuration. In one embodiment, they are configured as three-sided pyramids or as four-sided pyramids.

The hard metal element 42 has two side edges 112 and 114 extending transversely to the tool side face 104. In embodiments as they are depicted, in particular, in FIGS. 9 to 11, a respective chamfer 116 and 118 is formed in the transition region of the tool side face 104 and the respective side edges 112 and 114.

An angle 120 that is enclosed between the tool side face 104 on the one hand and the plane delimiting the chamfer 116 or 118 on the other hand is in a range of about 35° to about 550°.

In some embodiments the chamfers 116 and 118 extend in parallel to one another and in other embodiments they extend toward one another in the direction toward a distal end 122 of the tool side face 104.

The hard metal element 42 has a coupling projection soldering face 124 in the region of the coupling projection 92 for placing against the coupling receptacle abutment face. As is depicted in particular in FIGS. 2 to 4, the coupling projection soldering face 124 is located opposite the transverse bore 88 passing through the coupling receptacle abutment face 94.

The production of the semi-finished instrument 52 is described in more detail in the following in connection with FIGS. 2 to 5.

The hard metal element 42 is inserted into the recess 38 as already described, namely in such a way that the coupling projection 92 engages into the coupling receptacle 90 in a positive-locking manner. An end edge 126 of the hard metal element 42 pointing in the proximal direction then abuts against the first end face 60 or is separated therefrom by a narrow gap. An end edge 128 of the coupling projection 92 pointing in the distal direction abuts against the second end face 62 in a similar manner.

The solder chamber 68 is filled with the pasty solder 70 commencing from the end 72. For this purpose, for example as depicted in FIG. 4, a spout 130 of a tube 132 filled with solder 70 is plugged into the bore 78 and the solder 70 is pushed into the solder chamber 68.

The solder chamber 68 is dimensioned such that it can accommodate exactly the amount of solder 70 that is required to solder the hard metal element 42 and the instrument body part blank 54 without excess.

The soldering takes place under high temperature in a vacuum, namely in a hardening furnace at about 1000° Celsius. The solder 70 is drawn from the solder chamber 68 into the solder gap 100 as a result of the capillary action of the solder gap 100. At the end of the solder gap 100, i.e. between the first end face 60 and the end edge 126, the capillary action wears off and the solder no longer flows. The flow of solder is interrupted all around, i.e. between the side edges 112 and 114 and the abutment face 58. Unlike in the prior art, this results in there being no uncontrolled flow of solder, such that both the coating with solder stop and a generous overhang of the hard metal element 42 over the instrument body part blank 54 can be forgone.

The hard metal element 42 has its final form aside from the coupling projection 90. As described, chamfers 116 and 118 can already be formed on the hard metal element 42 before soldering, such that the manual chamfering of the hard metal element 42 after soldering to the instrument body part blank 54 can also be forgone.

As a result of the positive-locking engagement of the coupling projection 92 into the coupling receptacle 90 as well as the particular design of the first end face 60, which is formed corresponding to the end edge 126, a defined positioning between the hard metal element 42 and the instrument body part blank 54 can be ensured, thereby making possible to largely prevent a displacement thereof relative to one another during soldering.

After soldering, the solder chamber portion 74 is separated from the instrument body part blank 54. To facilitate this, a predetermined breaking point 134 is formed at which the solder chamber portion can be separated or snapped off by applying force. The coupling projection 92 is then also separated from the hard metal element 42 with the solder chamber portion 74.

After separating off the solder chamber portion 74 and the coupling projection 92, the distal end of the instrument body part blank 54 and of the hard metal element 42 is finished by grinding and polishing.

The semi-finished instrument 52 is now completed and can be movably coupled as an instrument body part 14 together with a further instrument body part 16, which is configured in the described manner, i.e. is equipped with the hard metal element 44, to form the instrument 10.

In one embodiment, the predetermined breaking point 134 is configured in the form of a weakened region 136, namely between the end 46 of the instrument body part 14 and the solder chamber portion 74.

The instrument body part blank 54 is formed by cold- or hot-forming.

In order to simplify the separation of the coupling projection 92 from the hard metal element 42, a thickness of the coupling projection 92, in particular an average thickness, is smaller than in the region of the tool side face 104.

Depicted in FIG. 6 is an embodiment with a tool element 42 that is of structured configuration and has a plurality of projections 108 and depressions 110, which are arranged or formed regularly.

In contrast to this, in the embodiment of the hard metal element 42 depicted in FIGS. 4 and 5, the tool side face 104 is of planar or microstructured configuration.

Depicted as an example in FIG. 7 is an embodiment of a hard metal element 42, which has no coupling projection 92. The end edge 128 is concavely curved pointing in the distal direction and transitions into the side edges 112 and 114 in a kink- or edge-free manner. The end edge 126 is of planar configuration. In particular, it may be formed slightly inclined in relation to the soldering face 98 in order to engage into an undercut formed on the recess 38. Due to the differently shaped end edges 126 and 128, which correspond to end faces 16 and 62 on an embodiment of an instrument body part blank 54 that is not depicted in the Figures, a defined positioning of the hard metal element 42 during soldering to the instrument body part blank 54 can also be achieved.

The hard metal element 42 depicted in FIG. 7 has a structure 106 such that said hard metal element 42 can be arranged both on the instrument body part 14 and on the instrument body part 16. The depressions 110 and projections 108 then correspondingly interengage with one another. Thus, only one single kind of hard metal element 42 is required to form the semi-finished instruments 52 for forming the instrument body parts 14 and 16.

Further embodiments of hard metal elements 42 are depicted as examples in FIGS. 9 to 11. They differ, in particular, in the configuration of the end edge 126.

In the embodiment of FIG. 9, the end edge 126 defines an angled form with two end edge portions 138 and 140, which extend transversely to the soldering face 98 and are inclined toward one another, such that a tip 142 pointing in the proximal direction is formed.

In the embodiment of FIG. 10, the end edge 126 is concavely curved pointing in the proximal direction.

In the embodiment of FIG. 11, the end edge 126 is planar, but encloses with the soldering face 98 an angle 144 that is smaller than 90°, in particular in a range between about 60° and nearly 90°.

As is schematically depicted in FIG. 12, this beveled end edge 126 can engage into an undercut 146 of the recess 38. The undercut 146 is delimited by the first end face 60 and the abutment face 58. The angle 144 ideally coincides with the angle defined by the undercut 146.

An undercut as defined in connection with FIGS. 11 and 12 may also be provided with the other hard metal elements 42 and 44 described above, namely optionally on the proximal or on the distal end thereof.

As a result of the formation of an external solder chamber 68 on the instrument body part blank 54 as described above, which is removed after soldering the hard metal elements 42 and 44 to the instrument body part blank 54, a weakening of the finished mouth parts 34 and 36 can be prevented. As described, an exact dosing and control of the flow of solder by capillary action to the desired connecting face is possible.

The solder chamber 68 can be removed in a simple manner as described if a predetermined breaking point 134 is provided for this purpose, for example by means of a tapering or constriction between the solder chamber portion 74 and a distal end of the recess 38 or 40.

The proposed further development also makes it possible to produce ready-to-install hard metal elements with tool-specific geometry that do not have to be significantly further processed after soldering to the respective instrument body part blank 54.

As a result of the proposed approach, a higher product quality can be achieved through improved process security and a reduction of manual work steps. This is associated with a reduction of production costs, in particular by being able to reduce waste and workload. An important advantage is also that corrosion problems of instruments with the user that are production-related, namely as described at the outset as a result of conventional soldering methods, can be prevented. Moreover, a higher stability of the instruments 10 can be achieved by reducing stress peaks and a concomitant risk of breakage can be reduced.

The invention claimed is:

1. A semi-finished instrument comprising:
   an instrument body part blank for forming an instrument body part of a medical instrument, said instrument body part blank being made of a metal;
   a distal end region; and
   a recess on the distal end region for accommodating a hard metal element,
   wherein:
   the recess has an abutment face for the hard metal element,
   the instrument body part blank comprises a solder chamber for accommodating solder
   the solder chamber is fluidically connected to the recess, and
   the instrument body part blank comprises a solder chamber portion, wherein the solder chamber is arranged or formed on the solder chamber portion, and wherein the solder chamber portion is configured so as to be separable from the instrument body part blank.

2. The semi-finished instrument according to claim 1, further comprising the hard metal element.

3. The semi-finished instrument according to claim 2, wherein at least one of:
   a) the hard metal element has a platelet-shaped configuration;
   b) the hard metal element comprises a soldering face for placing against the abutment face; or
   c) the hard metal element is inserted into the recess and connected to the instrument body part blank by soldering.

4. The semi-finished instrument according to claim 2, wherein:
   the hard metal element has a tool side face and a soldering face,
   the tool side face and the soldering face point in opposite directions, and
   the hard metal element has at least one side edge extending transversely to the tool side face, and wherein a chamfer is formed in a transition region of the tool side face and the at least one side edge.

5. The semi-finished instrument according to claim 2, wherein a coupling receptacle is formed on the instrument body part blank for accommodating a coupling projection that projects from the hard metal element.

6. The semi-finished instrument according to claim 5, wherein at least one of:
   a) the coupling receptacle is arranged or formed on the solder chamber portion;
   b) the coupling projection is separable from the hard metal element; or
   c) the coupling receptacle has a coupling receptacle abutment face, wherein the coupling projection has a coupling projection soldering face for placing against the coupling receptacle abutment face.

7. The semi-finished instrument according to claim 1, wherein at least one of:
   a) the solder chamber comprises a bore or is configured in the form of a bore; or
   b) the solder chamber is arranged or formed on a distal end of the instrument body part blank.

8. The semi-finished instrument according to claim 1, wherein the solder chamber defines a solder chamber longitudinal axis, wherein the recess defines a recess longitudinal axis, and wherein the solder chamber longitudinal axis and the recess longitudinal axis extend in parallel or substantially in parallel to one another.

9. The semi-finished instrument according to claim 8, wherein the solder chamber is fluidically connected to the recess by way of a transverse connection that extends transversely to the solder chamber longitudinal axis.

10. The semi-finished instrument according to claim 1, wherein the recess has a first end face and a second end face, wherein the first end face extends transversely to the abutment face, wherein the second end face extends transversely to the abutment face, and wherein the first end face and the second end face point toward one another or substantially toward one another.

11. The semi-finished instrument according to claim 10, wherein a contour of the first end face and a contour of the second end face differ from one another.

12. The semi-finished instrument according to claim 10, wherein the first end face and/or the second end face are of planar or substantially planar configuration or are concavely curved facing toward one another.

13. The semi-finished instrument according to claim 1, wherein at least one of:
   a) the instrument body part blank comprises a predetermined breaking point configured for separating the solder chamber from the instrument body part blank; or
   b) the instrument body part blank is formed by cold- or hot-forming.

14. A medical instrument comprising:
   at least one instrument body part made from a semi-finished instrument, said semi-finished instrument comprising an instrument body part blank made of a metal;
   a distal end region; and
   a recess on the distal end region for accommodating a hard metal element,
   the recess comprising an abutment face for the hard metal element,
   the instrument body part blank comprising a solder chamber for accommodating solder,
   the solder chamber being fluidically connected to the recess, and
   the instrument body part blank comprising a solder chamber portion, wherein the solder chamber is arranged or formed on the solder chamber portion, and wherein the solder chamber portion is configured so as to be separable from the instrument body part blank.

15. The medical instrument according to claim 14, further comprising at least one hard metal element, wherein the at least one hard metal element and the at least one instrument body part are connected to one another by solder extending to the solder chamber, and wherein the solder chamber is positioned between a distal end of the at least one hard metal element, and a distal end of the at least one instrument body part.

16. The medical instrument according to claim 14, wherein the at least one instrument body part comprises two instrument body parts formed as branches that are movably coupled to one another.

17. The medical instrument according to claim 16, further comprising at least one hard metal element, wherein the at least one hard metal element comprises a first hard metal element and a second hard metal element of identical configuration.

18. The medical instrument according to claim 17, wherein tool side faces of the first hard metal element and of the second hard metal element each have a macroscopic structure, in each case with a plurality of projections and depressions formed therebetween, wherein the plurality of projections of the first hard metal element engage into the depressions of the second hard metal element in a maximally proximate position of the first hard metal element and the second hard metal element, and wherein outer contours of the first hard metal element and the second hard metal element cover one another congruently or substantially congruently in the maximally proximate position.

19. A semi-finished instrument comprising:
an instrument body part blank for forming an instrument body part of a medical instrument, said instrument body part blank being made of a metal;
a distal end region; and
a recess on the distal end region for accommodating a hard metal element,
wherein:
the recess has an abutment face for the hard metal element,
the instrument body part blank comprises a solder chamber for accommodating solder, and
the solder chamber is fluidically connected to the recess, wherein the solder chamber defines a solder chamber longitudinal axis, wherein the recess defines a recess longitudinal axis, and wherein the solder chamber longitudinal axis and the recess longitudinal axis extend in parallel or substantially in parallel to one another.

20. The semi-finished instrument according to claim 19, wherein the solder chamber is fluidically connected to the recess by way of a transverse connection that extends transversely to the solder chamber longitudinal axis.

\* \* \* \* \*